United States Patent
Wallenås et al.

(10) Patent No.: US 11,583,621 B2
(45) Date of Patent: Feb. 21, 2023

(54) CARTRIDGE AND APPARATUS FOR PERFORMING ADSORPTION DIALYSIS

(71) Applicant: TRIOMED AB, Lund (SE)

(72) Inventors: Anders Wallenås, Lomma (SE); Nina Meinander, Södra Sandby (SE); Carin Malmborg, Höör (SE); Stefan Landholm, Malmö (SE); Hans Bengtsson, Eslöv (SE)

(73) Assignee: TRIOMED AB, Lund (SE)

( * ) Notice: Subject to any disclaimer, the term of this patent is extended or adjusted under 35 U.S.C. 154(b) by 258 days.

(21) Appl. No.: 15/577,241

(22) PCT Filed: May 27, 2016

(86) PCT No.: PCT/SE2016/000026
§ 371 (c)(1),
(2) Date: Nov. 27, 2017

(87) PCT Pub. No.: WO2016/190794
PCT Pub. Date: Dec. 1, 2016

(65) Prior Publication Data
US 2018/0140765 A1    May 24, 2018

(30) Foreign Application Priority Data
May 27, 2015    (SE) .................... 1530076-7

(51) Int. Cl.
*B01J 20/28*    (2006.01)
*B01J 20/20*    (2006.01)
(Continued)

(52) U.S. Cl.
CPC .......... *A61M 1/288* (2014.02); *A61M 1/1696* (2013.01); *B01J 20/20* (2013.01);
(Continued)

(58) Field of Classification Search
None
See application file for complete search history.

(56) References Cited

U.S. PATENT DOCUMENTS

| 4,031,010 A | 6/1977 | Nose |
| 4,213,859 A * | 7/1980 | Smakman ............... A61K 33/00 210/259 |
| 5,460,446 A * | 10/1995 | Chevallet ............ A61M 1/1656 137/205 |
| 6,408,894 B1 | 6/2002 | Davankov |

(Continued)

FOREIGN PATENT DOCUMENTS

| DE | 198 01 107 A1 | 7/1999 |
| DE | 101 57 569 A1 | 6/2003 |

(Continued)

OTHER PUBLICATIONS

Encyclopedia Britannica, "Elasticity," Jul. 7, 2015, accessed on the Internet at https://web.archive.org/web/20150707080300/http://www.britannica.com:80/print/article/182035, on Sep. 6, 2021, 6 pages. (Year: 2015).*

*Primary Examiner* — Hayden Brewster
(74) *Attorney, Agent, or Firm* — Birch, Stewart, Kolasch & Birch, LLP

(57) ABSTRACT

A cartridge to be used for adsorption dialysis. A container having flexible walls are arranged to provide an inner space enclosing adsorption powder, comprising activated carbon, a phosphate adsorbent and a potassium ion adsorbent and other adsorbents. A sufficient amount of activated carbon is provided for adsorption of urea by the activated carbon. The cartridge forms a vacuum-packed transportation cartridge by generating a sub-pressure in the inner space, whereby the powder particles are immobilized and the cartridge becomes stiff. Before use, the cartridge is primed by introducing a liquid into the inner space, which introduction takes place at a low pressure. During use, dialysis solution is circulated through the cartridge, which is still exposed to a sub-pressure, whereby the flexible walls are sucked against the (Continued)

powder material. A peritoneal dialysis circuit comprises a filter, in which a primary circuit is formed with the filter and the peritoneal cavity and a secondary circuit is formed with the filter and the adsorbent cartridge.

11 Claims, 5 Drawing Sheets

(51) Int. Cl.
  *B01J 20/22* (2006.01)
  *A61M 1/28* (2006.01)
  *A61M 1/16* (2006.01)
  *B01J 45/00* (2006.01)

(52) U.S. Cl.
  CPC ......... *B01J 20/22* (2013.01); *B01J 20/28052* (2013.01); *B01J 45/00* (2013.01); *A61M 1/287* (2013.01); *A61M 2202/0498* (2013.01); *A61M 2205/15* (2013.01); *A61M 2205/3331* (2013.01); *A61M 2205/50* (2013.01); *B01J 2220/62* (2013.01)

(56) References Cited

U.S. PATENT DOCUMENTS

| | | | |
|---|---|---|---|
| 7,850,635 B2 * | 12/2010 | Polaschegg | B01D 61/00 604/6.09 |
| 2005/0031509 A1 | 2/2005 | D'Ayot et al. | |
| 2007/0138183 A1 | 6/2007 | Ritter | |
| 2008/0135480 A1 | 6/2008 | Dumont D'Ayot et al. | |
| 2011/0120946 A1 | 5/2011 | Levin et al. | |
| 2012/0291891 A1 | 11/2012 | Ritter et al. | |
| 2013/0190681 A1 * | 7/2013 | Jansson | A61J 1/2093 604/28 |
| 2015/0029817 A1 | 1/2015 | Orszullok | |
| 2015/0144542 A1 * | 5/2015 | Pudil | B01J 20/3433 210/87 |

FOREIGN PATENT DOCUMENTS

| | | | | |
|---|---|---|---|---|
| GB | 1470 206 A | 4/1977 | | |
| WO | WO 97/38743 A1 | 10/1997 | | |
| WO | WO 99/06083 A1 | 2/1999 | | |
| WO | WO 2014/081368 A1 | 5/2014 | | |
| WO | WO 2014/081369 A1 | 5/2014 | | |
| WO | WO-2014081368 A1 * | 5/2014 | | A61M 1/16 |
| WO | WO 2015/000666 A1 | 1/2015 | | |

* cited by examiner

CARTRIDGE AND APPARATUS FOR PERFORMING ADSORPTION DIALYSIS

FIELD OF INVENTION

The present invention relates to a cartridge for performing adsorption dialysis and an apparatus and method for performing adsorption dialysis.

BACKGROUND

In absence of normal kidney function, renal disease patients require dialysis for removal of unwanted blood substances and for keeping water balance. Such dialysis may be used in the waiting time before a kidney transplantation or during the rest of the life of the patient.

Renal disease patients having a residual kidney function are often recommended peritoneal dialysis, because the residual kidney function may be maintained longer. End-stage renal disease patients may be treated by hemodialysis or alternatively peritoneal dialysis.

During such dialysis, large amount of dialysis fluid is used and discarded. Adsorption dialysis offers an attractive way of reducing the large amount of dialysis fluid by regenerating and reusing the spent dialysis fluid.

During adsorption dialysis, dialysis fluid is passed through an adsorption column comprising adsorbent material. Such material may be in powder form.

Adsorption dialysis can be used in hemodialysis, wherein the spent dialysate at the outer side of the dialyzer is passed through the adsorption column and waste substances are adsorbed. In another mode, the spent dialysate is passed through an inner space of an auxiliary dialyzer, wherein a purification fluid is passed through an outer filter space of the auxiliary dialyzer for removal of unwanted substances from the dialysate fluid. The purification fluid is passed through the adsorbent material.

Adsorbent dialysis can also be used in peritoneal dialysis. The dialysis fluid is removed from the peritoneal cavity and passed through the adsorbent material and returned to the patient. In an alternative mode, the dialysis fluid is passed through an inner space of a filter or dialyzer, wherein an purification fluid is passed through an outer filter space of the filter for removal of unwanted substances from the dialysis fluid. The purification fluid is passed through the adsorbent material.

Most adsorbent dialysis systems use urease for decomposition of urea into ammonium and carbon dioxide, whereupon the ammonium is adsorbed. This process is difficult to control, and there is a risk that ammonium enters the body via the dialysis fluid, which is undesirable. There is a need in the art for an adsorbent dialysis system, which does not use urease for removal of urea.

Most adsorbent columns use activated carbon, which is efficient for removal of creatinine, uric acid and other organic molecules. In addition, some heavy metals (trace substances) are adsorbed. However, urea is poorly adsorbed. In addition, leakage of heavy metals and emission of particulate carbon may be a problem.

The adsorbent column is normally transported with the powders in a dry state. The powders are sensitive to wear and tear, and activated carbon particles may easily be disintegrated during transportation, which is undesirable.

Before use, the powder cartridge needs to be primed. Activated carbon is often hydrophobic, which makes it difficult to wet the powder during the priming step. In addition, there is a risk of enclosing air pockets in the column during priming.

Patent document US4031010A1 discloses a combined dialyzer and adsorber unit in one disposable package. The dialyzer is integral with the adsorber which contains a chemical adsorbent to regenerate a dialysate solution. In a preferred embodiment the dialyzer is mounted in the form of a sleeve around the adsorber container as a core. Dialysate is introduced into the dialyzer, then immediately circulated through the chemical adsorbent contained in the adsorber. There the major components of the impurities dialyzed out from the dialyzer can be adsorbed, whereby the dialysate is regenerated. The sleeve can be the adsorber and the core the dialyzer.

During use of the column or adsorber unit, there is a risk that preferential flow paths or tunnels are formed inside the powder and between the column walls and the powder. Such preferential flow paths decrease the efficiency.

SUMMARY OF THE INVENTION

Accordingly, an object of the present invention is to mitigate, alleviate or eliminate one or more of the above-identified deficiencies and disadvantages singly or in any combination. Other objects appear from the description below.

In an aspect, there is provided a cartridge for dialysis, comprising a container having an interior space with variable volume, which comprises a powder material for adsorbent dialysis, wherein the container comprises at least a portion made of a flexible material, and wherein said interior space of the container comprises a sub-pressure in relation to the ambient pressure during use. The adsorbent material may comprise activated carbon.

In an embodiment, there may be arranged a pressure reducing valve at an inlet of the cartridge for lowering the pressure at the inlet line of the cartridge. The pressure reducing valve may be arranged integrally with said cartridge. The pressure reducing valve may be arranged to reduce pressure by at least 50 mbar. The pressure reducing valve may be adjustable for reducing pressure by 50 mbar, 100 mbar, 150 mbar, 200 mbar or 500 mbar at passage of a liquid through said pressure reducing valve.

In a further embodiment, the cartridge may be primed with a fluid before use in a dialysis treatment system, wherein such priming takes place at a sub-pressure in relation to the ambient pressure. Adsorption dialysis may take place by circulation of purification fluid through the cartridge with a sub-pressure in said interior cartridge space, which sub-pressure is at least about 50 mbar below ambient pressure.

In another aspect, there is provided an apparatus for performing dialysis, comprising a cartridge as mentioned above, and a pump for passing a purification fluid through the cartridge for adsorption dialysis by circulation of said purification fluid through the cartridge at a sub-pressure in said interior space, which sub-pressure is at least about 50 mbar below ambient pressure.

In a further aspect, there is provided a cartridge as mentioned above, wherein said powder material is a phosphate binding resin, comprising a polystyrene-based resin having an immobilized metal ion, the phosphate salt of which has a low solubility, and thus is capable of capturing phosphate. The metal ion may be immobilized by a metal chelating ligand, which may comprise iminodiacetic acid, which may form a complex with the metal ion. The metal ion may be lanthanum ($La^{3+}$) or ferric ion ($Fe^{2+}$ or $Fe^{3+}$).

In another embodiment, the polystyrene resin with iminodiacetic acid ligand may be provided in a first form comprising hydrogen ions bound to the chelating site and in a second form comprising sodium ions bound to the chelating site, wherein said first form and said second form are combined in a ratio between said first form and said second form for counteracting an elevation of the pH of the dialysis fluid when contacted with the carbon powder material.

In a further embodiment, there is further provided a second polystyrene resin comprising iminodiacetic acid (IDA) ligand without a metal ion immobilized, for adsorption of any metal ion leaking out of said first iminodiacetic acid (IDA)-metal complex, which second polystyrene resin is arranged downstream of said first polystyrene resin with iminodiacetic acid (IDA) ligand, which has formed a complex with the metal ion (M).

BRIEF DESCRIPTION OF THE DRAWINGS

Further objects, features and advantages of the invention will become apparent from the following detailed description of embodiments of the invention with reference to the drawings, in which.

DETAILED DESCRIPTION OF EMBODIMENTS

Below, several embodiments of the invention will be described. These embodiments are described in illustrating purpose in order to enable a skilled person to carry out the invention and to disclose the best mode. However, such embodiments do not limit the scope of the invention. Moreover, certain combinations of features are shown and discussed. However, other combinations of the different features are possible within the scope of the invention.

An adsorption based peritoneal dialysis system requires one or several cartridges for adsorption of substances from a peritoneal dialysis fluid which is instilled in the patient and removed from the patient.

Figure 1:
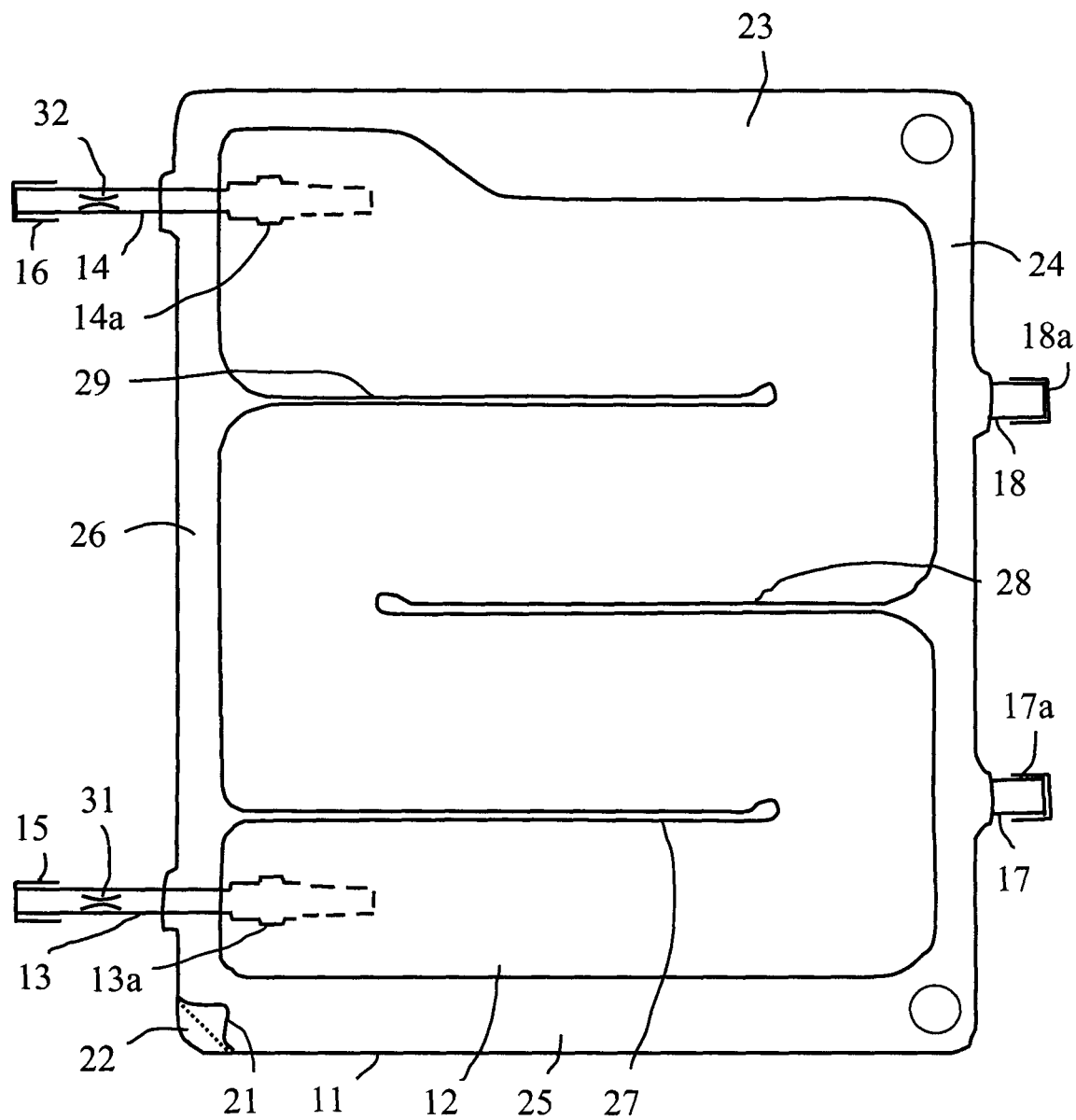
FIG. 1 is a plan view of an embodiment of a cartridge comprising adsorbent material.

FIG. 1 shows an adsorption cartridge 11 according to an embodiment of the invention. The cartridge encloses adsorbent material 12. An inlet tube 13 and an outlet tube 14 conduct fluid into and out of the cartridge for passage of fluid through the adsorbent material. In FIG. 1 the inlet tube 13 and the outlet tube 14 are sealed by lids 15 and 16. Two further tubes 17 and 18 are arranged in the cartridge for initial introduction of adsorbent material in the cartridge.

The cartridge according to the embodiment shown in FIG. 1 is rectangular and comprises two plastic sheets 21, 22, which are sealed to each other by sealing welds 23, 24, 25, 26 along the edges. In addition there are sealing welds 27, 28, 29 arranged so that a meander-like space is formed inside the cartridge. Other designs are possible. Alternatively, the bottom plastic sheet 22 may be replaced by a sheet of a rigid material and the top plastic sheet 21 may be made from a flexible material.

The plastic sheets are flexible and substantially non-elastic. Thus, if a fluid is introduced under pressure, the meander-like space if inflated and forms four substantially cylindrical spaces connected in series.

The tubes 13, 14, 17, 18 are passed through the welding in a sealed manner during the welding procedure. The tubes 13 and 14 are initially closed as shown.

A nozzle is inserted through the lower tube 17 and an adsorbent powder is introduced into the lower first cylindrical space between the edge welding 25 and the intermediate welding 27. Then, the nozzle is redirected into the second lower space between welding 27 and welding 28 and adsorbent powder is introduced into this space until it is filled. The same process is repeated via the upper tube 18, whereby the third cylindrical space between welding 28 and welding 29 is filled, followed by the fourth cylindrical space between welding 29 and the edge welding 23. In this manner the entire inner space of the cartridge is filled with adsorbent powder.

In an embodiment, the powder is a dry powder and the cartridge is filled in a dry state. The powder is filled up so that substantially all space is occupied by the powder.

If required, the cartridge may be shaken or turned upside down several times in order to uniformly distribute and pack the powder.

If there are several different powder materials, such materials may be arranged in a desired order along the meander-like flow path. Alternatively, the powder materials may be mixed.

After filling the cartridge, the contents inside the cartridge is exposed to a vacuum, resulting in that the powder particles are pressed towards each other. In addition, the plastic sheet material is sucked towards the particles. In this manner, a vacuum-packed, hard cartridge is formed, which can be conveniently transported in this shape. In addition, the cartridge is easily handled and operated for insertion into place in a dialysis equipment. Furthermore, the particles are fixed in relation to each other during transport and storage, meaning that the particles are not further disintegrated.

The tubes 17 and 18 are sealed after introduction of the powder. The tubes may be sealed by arranging lids 17a and 18a at the tubes and sealing the lids, for example by an adhesive or by heat welding. The tubes 17 and 18 may be used for providing the vacuum pressure before being sealed.

The vacuum pressure or sub-pressure required for obtaining a hard cartridge is not critical. Already a small sub-pressure may be sufficient. In order to have a safety margin, a sub-pressure of about 30 mbar below ambient pressure may be used. If a sub-pressure of 50 mbar or 100 mbar is provided, a safety margin is obtained.

However, according to embodiments of the present invention, a much lower sub-pressure is beneficial, such as 800 mbar or 900 mbar below ambient pressure, see further below.

Normally, the ambient pressure is atmospheric pressure. However, in some embodiments, ambient pressure may be a pressure which is higher or lower than atmospheric pressure. A hard and stiff cartridge is obtained when the pressure inside the cartridge is below the ambient pressure, whatever the ambient pressure is. It is important that all air inside the cartridge is expelled from the inside space.

The inlet tube 13 and the outlet tube 14 may be initially provided with break pins 31 and 32, which initially seal the tubes 13 and 14 in a gas-tight manner. When the break pins are broken the seal is opened and fluid can flow through the tubes. In some embodiments, the lids 15 and 16 may be unnecessary. In addition, at least the outlet tube 14 is provided with a filter 14a for preventing particles from leaving the cartridge. Such a filter 13a may as well be provided in the inlet tube 13.

There are several advantages of having the adsorbent cartridge in the nature of a vacuum-packed container or bag. The powder material will be protected against mechanical damage and will maintain the powder integrity. If there are several different powder materials they will not blend during the handling. The powder is dry and comprise only a small amount of air. The shelf-time may be improved. A hard vacuum-packed cartridge is more easy to handle. A damaged cartridge is easily indicated by loss of the vacuum pressure.

After transportation and possible shelf time and before use, the cartridge needs to be primed by introduction of a liquid into the cartridge, whereby the liquid contacts the powder and surrounds the powder and replaces the small amount of air still present inside the cartridge.

Such priming is performed by connecting the inlet tube 13 to a source of liquid and connecting the outlet tube 14 to a source of sub-pressure. Then, the break pins are broken and the liquid is allowed to enter through the inlet tube, while a sub-pressure is maintained at the outlet tube. When the cartridge is filled with liquid, the priming process is ready.

During the priming procedure, any air inside the powder particles decrease in volume as the pressure increase and liquid at least partly enters into the interior voids of a porous particle, which is expected to be beneficial for the adsorption properties. If for example the intitial pressure inside the cartridge is about 50 mBar (absolute pressure) and the pressure during priming increases to about 500 mBar, the air volume inside the pores of the particles decreases by a factor of 10, resulting in that the priming fluid enters about 90% of the voids inside each particle.

In an embodiment, the powder cartridge may comprise adsorbent material, such as activated carbon powder, see further below.

The powder material may be any adsorbent powder material used for adsorption dialysis. Examples of adsorbent materials are disclosed in for example the patent publications WO2009157877A1, WO2014007716A1, WO2014081367A1, WO2014081368A1, WO2014081369A1. Further examples are discussed below.

The cartridge may be used in a dialysis apparatus, for hemodialysis or peritoneal dialysis. Below will be described the use in a peritoneal dialysis apparatus.

Figure 2:
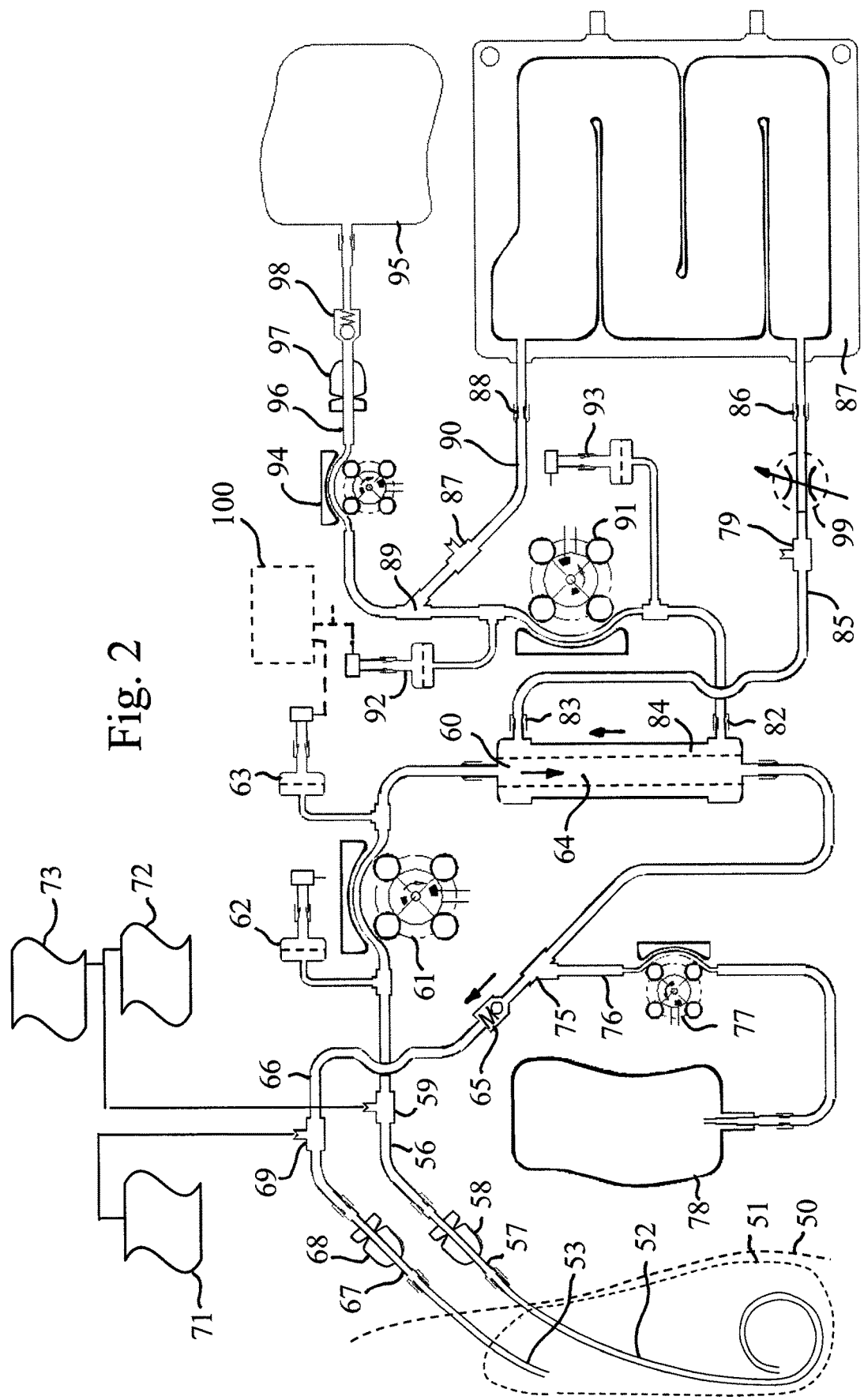
FIG. 2 is a schematic diagram of an embodiment of the apparatus according to the invention.
Figure 3:
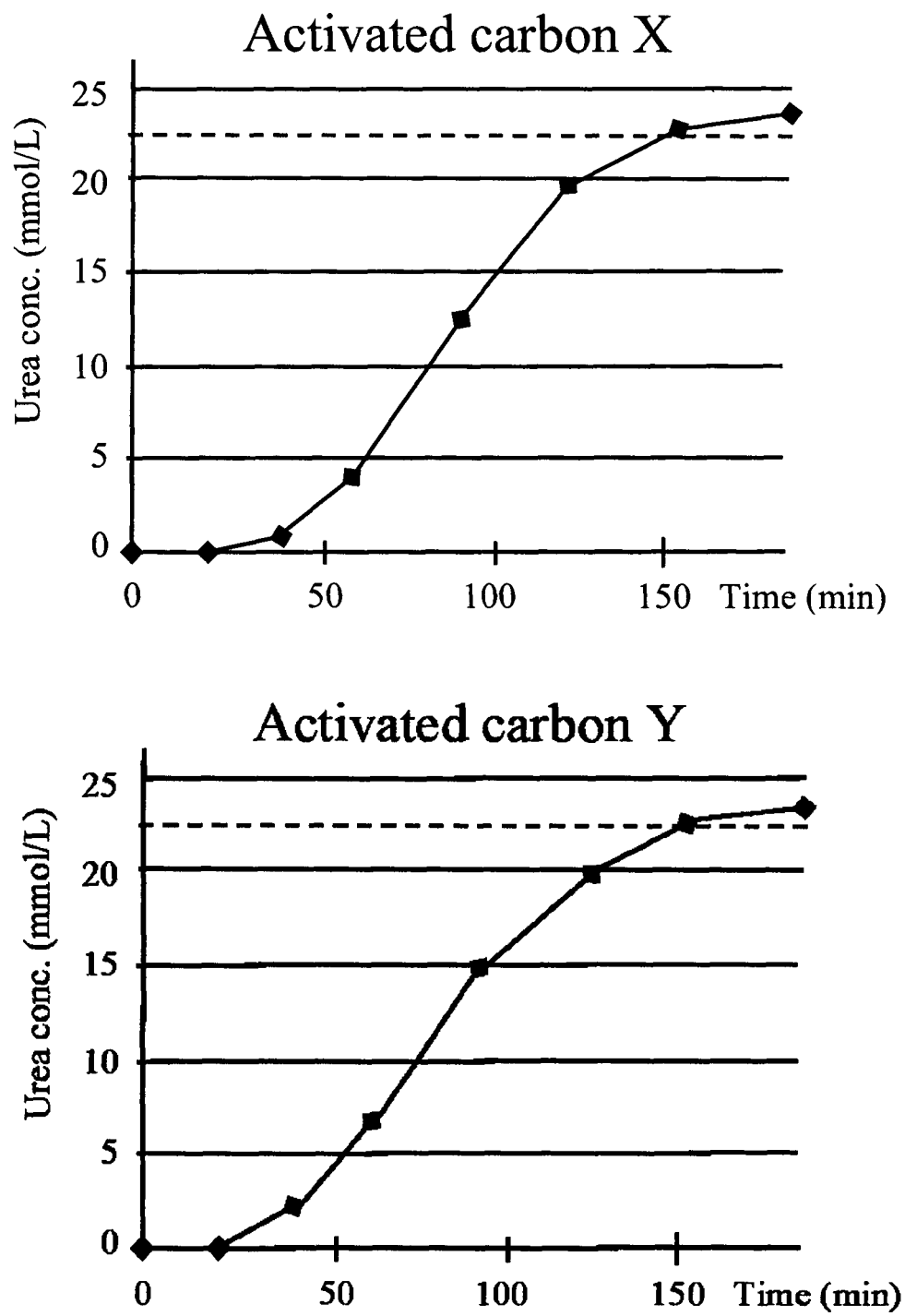
FIG. 3 is a diagram showing adsorption of urea to activated carbon.

FIG. 2 shows a schematic diagram of a peritoneal dialysis apparatus in which the cartridge according to FIG. 1 may be used.

To the left in FIG. 2, there is shown a peritoneal cavity 51 of a patient 50. Two catheters 52 and 53 are inserted in the peritoneal cavity for connection of the cavity to the peritoneal dialysis apparatus. The bottom catheter 52 is used for removal of peritoneal fluid from the cavity and the upper catheter 53 is used for supply of peritoneal fluid to the cavity. However, the opposite direction may alternatively be used. A double-lumen catheter may alternatively be used.

A removal line 56 for removal of dialysis fluid from the patient is connected to the lower catheter 52 via a clamp segment 57 comprising a manual clamp device 58 for opening and closing the connection between the removal line 56 and the lower catheter 52. The dialysis fluid passes through the removal line 56 to a patient pump 61 and further to an interior space 64 of a filter 60.

Two pressure gauges 62, 63 are arranged at each side of the patient pump 61 for measuring pressures at these positions. The interior space 64 of the filter 60 is a space inside hollow fibers, which makes up the filter. The filter may be a hollow fiber filter having a bundle of hollow fibers passing through an outer filter space. The interior space 64 of the filter is the interior of the hollow fibers. The filter may be a dialyzer.

From the interior space 64 of the filter, the fluid passes through a back-flow valve 65 and further to a return line 66 connected to the upper catheter 52 via a clamp segment 67 comprising a manual clamp device 68 for opening and closing the connection between the return line 66 and the upper catheter 53.

The return line 66 comprises a T-connector 75 just before the backflow valve 65. An additive fluid supply line 76 provides concentrated additive fluid to the return line 66 by means of a additive fluid pump 77 and an additive fluid supply bag 78.

The additive may be concentrated glucose solution, which is added for maintaining the glucose concentration constant in the peritoneal dialysis fluid returned to the patient. Other additives may also be provided to keep a constant concentration thereof, such as ions of bicarbonate, sodium, calcium, potassium, magnesium, etc.

Thus, the peritoneal fluid passing to the peritoneal cavity is continuously (or intermittently) replenished with glucose and/or other additives in order to keep the composition of the dialysis fluid substantially constant in the peritoneal cavity.

The removal line 56 comprises a T-connector 59 adjacent the connection to the lower catheter 52 and the return line 66 comprises a T-connector 69 adjacent the connection to the upper catheter 53. The T-connectors 59, 69 are used for connection of drain bags 71, 72 and a PD fluid supply bag 73.

An outside space 84 of the hollow fibers of the filter 60 is connected to an inlet connector 82 and an outlet connector 83 of the filter. The outlet connector 83 is connected to a cartridge inlet line 85, which is connected to an inlet connector 86 of the powder cartridge. An outlet connector 88 from the cartridge is connected to a T-connector 89 via a cartridge outlet line 90. The cartridge outlet line 90 returns fluid back to the inlet connector 82 of the filter by means of a purification fluid pump 91. Two pressure gauges 92, 93 are arranged at each side of the pump 91.

A drain pump 94 is connected to T-connector 89 for withdrawal of fluid from the system for passage through a drain line 96, via a manual clamp device 98 and a back-flow valve 97 to a drain bag 95.

Sample ports 87 and 79 may be arranged before and after the cartridge.

The normal operation of the apparatus is described below.

The peritoneal cavity is filled with dialysis fluid and exchange takes place of molecules, ions and substances with the blood. In addition, ultrafiltration takes place.

In a primary circuit, the dialysis fluid is withdrawn from the peritoneal cavity by means of pump 61 and the lower catheter 52 and the removal line 56 (the clamp 58 is open). The operation of pump 61 is monitored by pressure meters or pressure gauges 62 and 63. The dialysis fluid is passed through the interior space 64 of the hollow fibers of the filter 60. The dialysis fluid exits the filter and passes via return line 66 to the upper catheter 53 and further to the peritoneal cavity. A continuous supply of additive fluid is added by additive fluid pump 77 from the additive fluid bag 78. There may be several additives, having separate bags and metering pumps. Alternatively, all additives are included in one and the same bag and metered by one pump The expression "dialysis fluid" means any fluid passing in the primary circuit comprising the peritoneal cavity and the interior of the hollow fibers of the filter. The expression "purification fluid" means any fluid passing in a secondary circuit comprising the outside of the hollow fibers of the filter and the purification cartridge (see below).

Since there is a continuous circulation of dialysis fluid, an efficient exchange of substances takes place from the blood to the dialysis fluid (and in the opposite direction). In addition, the continuous supply of glucose (and/or other substances) makes the glucose concentration substantially constant in the peritoneal cavity. By adding the glucose after the filter, the amount of glucose (and/or other substances) lost in the filter is minimized.

In a secondary circuit, the purification fluid exits the outer filter space 84 via outlet 83. A suction pressure is generated by pump 91 and such suction pressure promotes passage of purification fluid from the outlet 83 of filter 60 via cartridge supply line 85 to the cartridge inlet connector 86. The purification fluid passes through the powder of the cartridge and to the outlet 88 and further via T-connector 89 and line 90 to the pump 91 and further to the inlet 82 of outer filter space 84. The purification fluid is regenerated in the cartridge by removal of unwanted ions and substances, as further discussed below. When the fluid passes along the hollow fibers at the outside thereof, unwanted substances in the dialysis fluid passes over the hollow fiber membrane to the purification fluid at the other side of the membrane by diffusion. In addition, convection of fluid across the filter hollow fiber membrane may take place.

Since the system is closed, the pressures will adjust themselves in dependence of the pressure in the peritoneal cavity. However, because of the concentration of glucose, an ultrafiltration will take place via the peritoneal membrane and the dialysis fluid volume in the peritoneal cavity will increases. This will be manifested by an increased pressure in pressure gauge 62 and also in pressure gauges 63 and 93.

Such an increase of pressure may counteract further ultrafiltration. In one embodiment, a drain pump 94 may be activated and may pump a predetermined volume of fluid out of the secondary circuit to a drain bag 95 via T-connector 89 and a drain line 96. Clamp 97 in the drain line 96 is open. When the volume in the secondary circuit decreases, some fluid will pass from the primary circuit through the hollow fiber membrane to the secondary circuit by convection, until balance is obtained.

The removal of fluid to the drain bag may take place two times per hour. Each time, a volume of 100 ml is removed. Other volumes and times may be used as decided by the physician. The removal may be continuous or intermittent.

Alternatively, the cartridge may be replaced after a time period of about 4 hours. The cartridge may have a fluid content of about 800 ml, which means that 800 ml of fluid is removed from the system each time a cartridge is replaced.

It is an object of the present embodiments to operate the powder cartridge under a constant sub-pressure, otherwise there is a risk that preferential flow paths are formed adjacent the flexible plastic sheets and elsewhere in the cartridge.

Since the pump 91 is arranged for suction of fluid through the cartridge, a sub-pressure is obtained by the flow resistances in the filter 60 and cartridge supply line 85. Such sub-pressure may be sufficient for preventing preferential flow paths.

In addition, a pressure reduction valve 99 may be arranged in the cartridge supply line 85. The pressure reduction valve 99 is arranged to open at a predetermined pressure of for example 50 mbar. Thus, it is assured that the cartridge is operated at a sub-pressure of at least 50 mbar below ambient pressure. In order to have a larger margin, the predetermined reduction pressure may be 100 mbar, or 150 mbar. During such conditions, the plastic sheets of the cartridge are sucked against the outer surface of the body of powder, resulting in that no preferential flow paths may be established. The sub-pressure is measured and monitored by pressure gauge 92. It is desired that the measured sub-pressure should be no more than 200 mbar below ambient pressure.

The pressure reduction valve 99 may be an adjustable pressure regulation valve, so that the opening pressure of the regulation valve may be adjusted. Such adjustment may be manual or automatic.

The pressure reduction valve may alternatively or additionally be arranged integrally with the cartridge.

A computer 100 is arranged to receive signals from the pressure gauges and from the pumps. The computer controls the operation of the pumps. Such arrangement is conventional.

When the dialysis session is over, dialysis fluid is removed from the patient, for example to drain bag 72, which is arranged in a low height position, so that dialysis fluid may be removed by gravity forces.

Before use, the dialysis apparatus should be exposed to a priming step, wherein all lines, tubes and devices are filled with liquid and all air is displaced from the system. The priming step takes place by connecting a priming fluid bag 73 and a drain bag 71 to the T-connectors 59 and 69 as shown in FIG. 2. The drain bag 72 is closed by a clamp. The patient is disconnected from the dialysis apparatus by closing clamps 58 and 68.

In a first step, pump 61 is operated and passes fluid from bag 73 to the inner space 64 of filter 60 and further via line 66 and backflow valve 65 to the drain bag 71. The pump 61 is operated at a low speed so that air inside the tubes and devices is displaced to the drain bag 71 and the tubes are washed by the fluid. Any contaminants are removed. The additive fluid pump 77 may be operated at the same time in order to displace any air in line 76.

After a predetermined time period, pump 91 is operated in its reverse direction and pump 94 is also operated in its normal direction, while clamp 97 is open. Cartridge 87 is closed since the break pins in connectors 86 and 88 are still closed. Fluid in the primary circuit passes through the semipermeable membrane of the filter to the secondary circuit and out via inlet 82 in a reverse direction and via line 90 and pump 91 and line 96 and pump 94 to drain bag 95. In this manner, air is removed from line 90 and the exterior space 84 of the filter. In this manner, the filter is completely free from any air inside the filter.

Finally, pump 91 is stopped and the break pins in connectors 86 and 88 are broken. The drain pump 94 may be stopped or may be running. Thus, the sub-pressure, which prevails inside the cartridge 87 is connected to cartridge supply line 85 and any air inside line 85 passes into the cartridge 87. Then, purification fluid starts to flow from the outlet 83 into line 85 and to the cartridge 87.

It is an advantage if the sub-pressure inside the cartridge before priming is low, much lower than is required for forming a vacuum-packed container. Thus, in an embodiment, there is provided a predetermined cartridge sub-pressure, such as 500 mbar, 800 mbar or 950 mbar below ambient pressure. The sub-pressure inside the cartridge is measured by the pressure gauge 92 as soon as break pin 32 is broken. If the cartridge sub-pressure is not sufficient, for example higher than 800 mbar below ambient pressure, the cartridge is declared having a leak and may be discarded.

The pump 94 can be operated to keep the pressure low at the outlet 88 of the cartridge, which is monitored by pressure meter 92. However, drain pump 94 may be a peristaltic pump, which is ineffective in pumping air at a low pressure. Thus, if the sub-pressure is not sufficient, it takes a long time for pump 94 to form a sub-pressure, and the drain pump may not be used for lowering the pressure.

Priming fluid enters the cartridge and surrounds the powder particles, still under a sub-pressure. Priming fluid passes slowly all the way from the inlet 86 to the outlet 88 and wets the powder particles and exits to the drain bag 95. When priming fluid exits the outlet 88 and reaches the pump 94, the secondary circuit is ready for use. However, a predetermined amount of priming fluid, such as about 200 ml, may first be flushed out to the drain bag in order to remove contaminants and other unwanted substances and products from the cartridge.

The priming fluid enters the cartridge via cartridge supply line 85 at a low pressure and air inside the cartridge is removed and the priming fluid surrounds the powder particles while they are exposed to said cartridge sub-pressure. When the pressure finally rises, for example from 950 mbar to 500 mbar below ambient pressure, the air pressure of the air still left inside the porous particles will increase from a low pressure to a higher pressure resulting in that the air volume inside such porous particles decreases. Since the powder particles are fully surrounded by priming fluid, such priming fluid will enter into the voids of the porous particles and contact the large inner surface of the particles. Thus, the priming fluid will have a large contact surface to the powder particles after priming at a sub-pressure and subsequent return to a higher pressure. Such improved wetting of the particles is expected to increase adsorption.

Such improved wetting is expected to be further improved if the sub-pressure is high, i.e. that the absolute pressure is low, such as 800 mbar below ambient pressure or lower (950 mbar), as mentioned above. When the pressure increases from an absolute pressure of 200 mbar to an absolute pressure of 800 mbar, any air volume inside the voids of the porous particles decreases by a factor of four, which promotes wetting of a large surface of the powder particle.

The priming step of the secondary circuit may take a long time, such as more than 20 minutes. Since it is desired to start peritoneal dialysis circulation as soon as possible, such circulation may start before the secondary circuit is entirely primed.

A convenient time to start peritoneal dialysis circulation is after the time when the filter is fully primed but before the time when the cartridge is fully primed. In the above sequence of steps, this time instance may be when the pump 91 stops its reverse operation and the cartridge break pins are broken and the cartridge priming starts.

The fluid bag 73 may comprise peritoneal dialysis fluid of a desired composition, which is well-known in the art. Now, the clamp 58 in the return line 56 is opened and dialysis fluid from bag 73 is allowed to enter the peritoneal cavity via gravity forces, since pump 61 is non-active. The clamp 68 in supply line 66 is also opened and any air and/or liquid inside the peritoneal cavity is allowed to escape to drain bag 71. As shown in FIG. 2, the fluid bag 73 is arranged at a height position so that the gravity forces generates the inflow of fluid.

After a predetermined time period, the pump 61 starts operation and starts to circulate the dialysis fluid out of the peritoneal cavity via removal line 56 and through the filter and via return line 66 back to the peritoneal cavity. The drain bag 71 is disconnected or clamped. Fluid bag 73 is still connected since fluid passes out from the primary circuit via the hollow fiber membranes to the secondary circuit in order to fill the cartridge with fluid. The arrangement of fluid bag 73 at a predetermined height position ensures that a positive pressure is maintained in the peritoneal cavity during the priming of the cartridge 87. The fluid bag 73 may be maintained until the cartridge is fully primed or may be removed when the pump 61 starts operation or any time there between.

When the cartridge 87 is primed, pump 91 is activated and pump 94 is stopped. Thus, purification fluid is circulated in the secondary circuit. As mentioned above, a predetermined amount of fluid may first be passed out to the drain bag 95.

The flow rate in the secondary circuit may be low, such as about 10 to 50 ml/min. At such a low flow, preferential paths through the powder material may not form. A sub-pressure relative to the ambient surrounding atmosphere and inside the cartridge is assured by flow resistances through the lines and/or by the additional pressure drop over pressure reduction valve 99. It is mentioned that the powder material in the cartridge does not dissolve or change in volume, which means that the powder particles may be kept immobilized by the subpressure inside the cartridge. However, some of the powder materials may swell during the priming, but remain at a substantially constant volume after priming and during the subsequent treatment.

During the priming step, the priming fluid is taken from the primary circuit and passes through the membrane of the hollow fibers to the secondary circuit. There is a large pressure drop across the membrane pores and such pressure drop will assist in keeping the inlet pressure to the cartridge low during the priming step. In addition, the pressure reduction valve 99 adds a pressure drop. These pressure drops add to maintain a low priming pressure of less than for example an absolute pressure of 200 mbar. After priming, when the pressure increases to for example an absolute pressure of 800 mbar, the air volume inside the voids of the porous particles decreases by a factor of four, which promotes wetting of a large surface of the powder particle.

Figure 4:
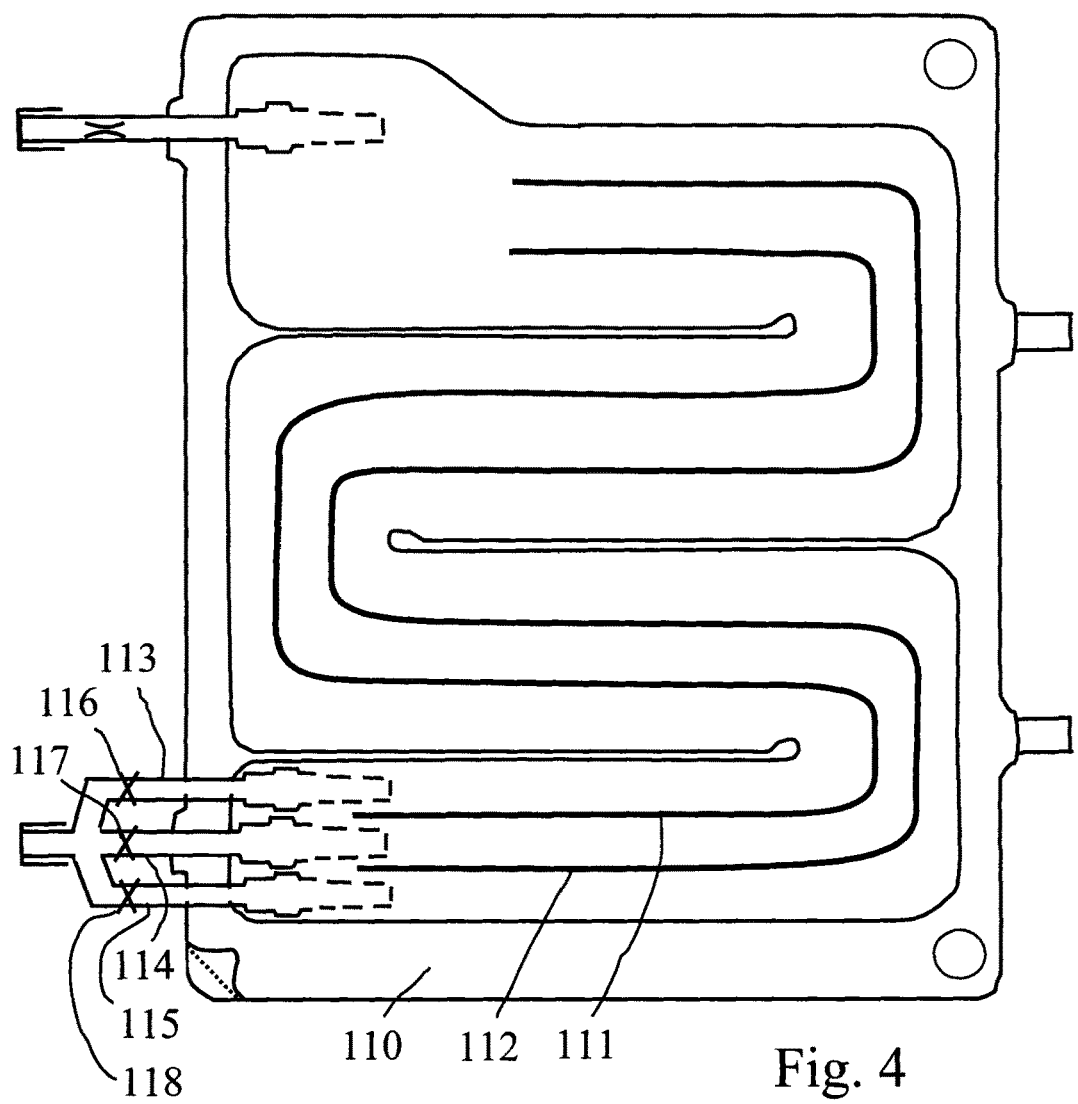
FIG. 4 is a plan view of another embodiment of a cartridge comprising adsorbent material.

In order to further decrease the formation of preferential paths in the cartridge, there may be arranged partition walls dividing the flow path through the cartridge in several flow channels, as shown in FIG. 4. The cartridge 110 shown in FIG. 4 comprises two partition walls 111, 112 which extend all the way from the inlet tube and almost to the outlet tube. In addition, there is provided three inlet tubes 113, 114, 115, which provide purification fluid to each separate channel, when a corresponding valve 116, 117, 118 is opened. The first valve 116 may be opened during the first 1 hour of a treatment, whereupon the first valve is closed and the second valve 117 is opened during the next hour and so on. In this manner, preferential paths are avoided, especially in the corners. In addition, the adsorption material is utilized more efficiently, especially the activated carbon particles. There may be one, two, three, four or five partition walls, or even still more.

Figure 6:
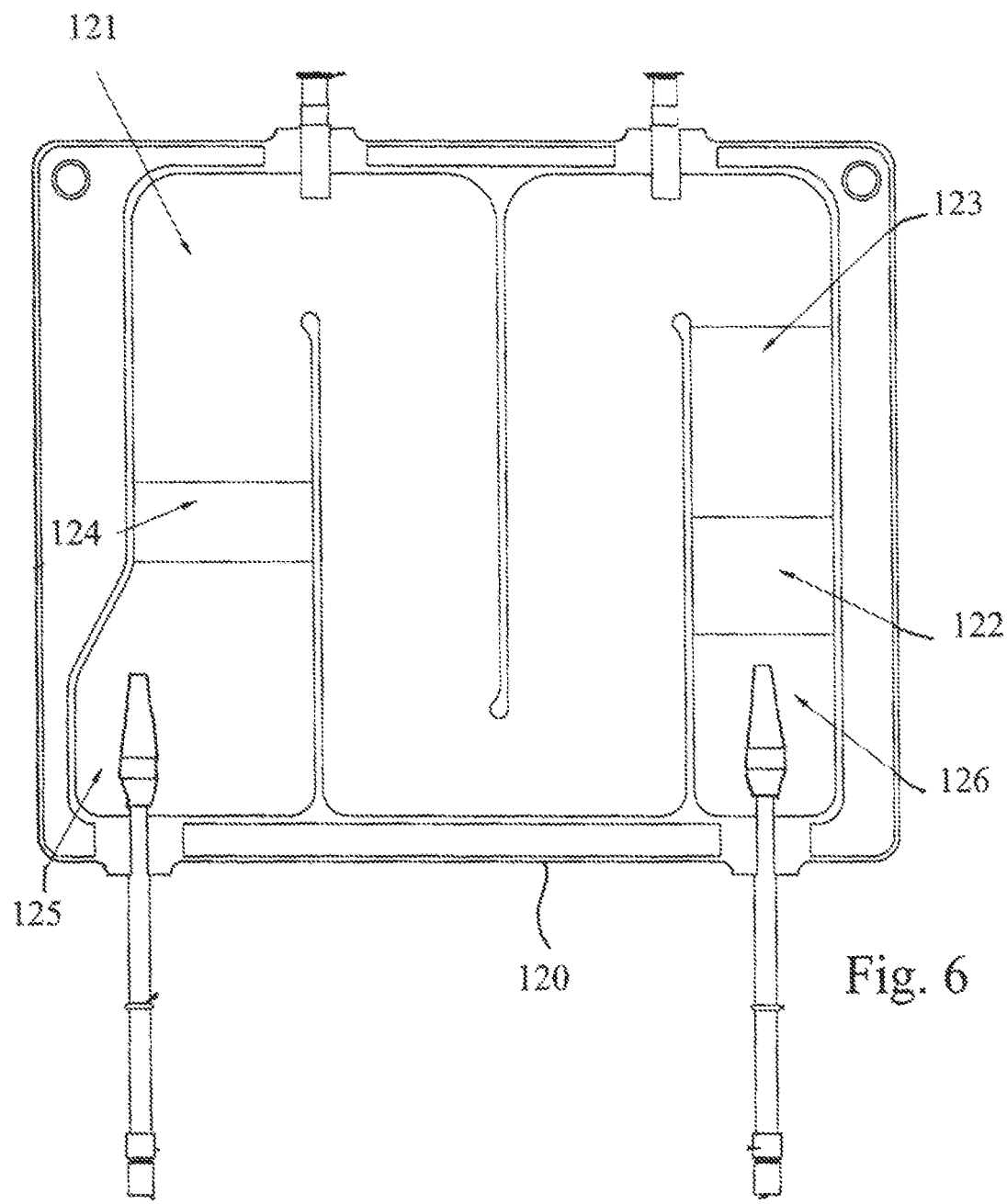
FIG. 6 is a plan view showing different powder materials in the cartridge.

In an embodiment of the cartridge 120, the adsorbent powder comprises activated carbon 121, a phosphate ion binding powder 122 and a potassium ion binding powder 123, see FIG. 6. In addition, there may be a metal chelating powder or material 124 for removal of heavy metals and other metals or metal ions. At the entrance and exit areas, there may be arranged additional activated carbon powder material 125, 126.

The powder particles does not need to be spherical but may have any shape. For example, the activated carbon (and other powder material) may be provided as flakes, rods, granulates, fibers or spherical particles. The powder material may be of different sizes.

It is known that activated carbon does adsorb a small amount of urea, see for example EP0013403A1. The cartridge according to embodiments is designed to comprise a sufficient amount of activated carbon for adsorbing urea in a peritoneal dialysis apparatus. Thus, the use of urease is no longer required for removal of urea.

Thus, a cartridge to be used for adsorption dialysis is provided according to embodiments. A plastic container is provided, which has flexible walls, which are arranged to provide an inner space enclosing adsorption powder, comprising activated carbon, a phosphate adsorbent and a potassium adsorbent and other adsorbents. A sufficient amount of activated carbon is provided for adsorption of urea by the activated carbon.

The cartridge forms a vacuum-sealed transportation package by providing a sub-pressure in the inner space, whereby the powder particles are immobilized and the cartridge becomes stiff.

After transportation and before use, the cartridge is primed by introduction of a liquid into the inner space, which introduction takes place at a low pressure.

During use, dialysis solution is circulated through the cartridge, which is still exposed to a sub-pressure, whereby the flexible walls are sucked against the powder material.

A peritoneal dialysis circuit comprises a filter, in which a primary circuit is formed comprising the filter and the peritoneal cavity and a secondary circuit is formed with the filter and the adsorbent cartridge.

The system may be used for hemodialysis by passing blood instead of peritoneal dialysis fluid to the filter. In this case, no glucose is added but other additives may be required, and conventional components in the blood path are used, such as air traps and other safety measures.

The cartridge may also be used for peritoneal dialysis without a filter, wherein the peritoneal dialysis fluid is passed directly through the cartridge.

The cartridge may be provided as a plastic bag as mentioned above. Other designs of the cartridge may be used, such as a container having some rigid walls and some flexible walls.

The flexible walls will ensure that the particles are compressed under the sub-pressure and the friction between the particles will result in a hard package.

The flexible walls may be non-elastic, which will facilitate filling of the cartridge and maintaining the shape thereof during filling. However, the walls may alternatively be elastic and the filling may take place in a mold. When the elastic walls are exposed to said sub-pressure, the package will become stiff and hard and form a vacuum-packed container or cartridge.

In an alternative embodiment, the sub-pressure in the vacuum-packed cartridge is only sufficient for keeping the cartridge stiff and hard, such as about 50 mbar below ambient pressure. The pump 94 may be replaced by a pump, which is able to generate a sub-pressure of about 800 mbar, such as a centrifugal pump. In this embodiment, the upper break pin 32 at the outlet of the cartridge is first broken, while pump 91 is non-active and pump 94 is active in order to lower the pressure inside the cartridge to an absolute pressure of about 200 mbar or 50 mbar. When a desired sub-pressure is obtained, as measured by pressure gauge 92, the second break pin 86 is opened and priming of the cartridge starts. When the cartridge is filled with liquid and the liquid reaches the pump 94, the sub-pressure is relieved to a sub-pressure of about 150 mbar or 500 mbar below ambient pressure, whereby the air inside the voids of the powder decrease in size as mentioned above.

The pressure regulation valve 99 may be operated in order to maintain a sufficient reduction pressure over the valve. Thus, the pressure regulation valve 99 may initially be adjusted to a reduction pressure of about 800 mbar, which is increased to for example 600 mbar in order to allow introduction of liquid in the cartridge. When the cartridge is filled with liquid, the regulation valve may be adjusted to 150 mbar.

In another alternative embodiment, the dialysis bag 73 is used as an accumulation bag. The bag 73 is arranged at a predetermined height position, for example about 30 cm above the upper catheter 53, which will be about the height position of the shoulder of the patient. The bag 73 is connected to the system all the time. If ultrafiltration results in that the volume of dialysis fluid increases, such increased volume may be accumulated in the bag 73.

When the cartridge is primed, the priming fluid is taken from the fluid accumulated in the bag 73. In this manner, a substantially constant pressure is maintained in the peritoneal cavity. Alternatively, the bag 73 may be connected and disconnected when needed.

When the cartridge is replaced, after for example 4 hours of use, the old cartridge is disconnected and a new vacuum-packed cartridge is connected. The new cartridge needs to be primed, whereby a volume of fluid is allowed to replace the air inside the cartridge as explained above. The volume of fluid is taken from the primary circuit, which means that any fluid, which has been ultrafiltrated from the patient is used for priming purpose. As mentioned above, a predetermined amount of fluid may be discarded, such as 200 ml, before the cartridge is connected to the filter in the secondary circuit flow.

The filter or dialyzer is effective in maintaining albumin and larger substances and cells out of contact with the adsorbent cartridge. Thus, albumin loss in the peritoneal dialysis is minimized.

The adsorbent dialysis may be performed during the day in four sessions of four hours each. Thereafter, the filter and the entire tube set is discarded and a new filter and tube set is used. Alternatively, the peritoneal dialysis may last for longer times, such as 24 hours or 36 hours or longer.

In another alternative mode, the peritoneal dialysis is performed during night time, when the patient is sleeping. In this mode, a larger cartridge may be used, since the patient is not moving, and no replacement of the cartridge takes place. In this mode, a continuous or intermittent removal of fluid to drain bag 95 may be appropriate.

Below, three examples of adsorption of urea to activated carbon are disclosed.

EXAMPLE I 5 g of three different activated carbons, A, B and C were weighed in 250 mL e-flasks. To each flask, 100 mL of spent dialysis fluid from a peritoneal dialysis patient, containing a concentration of 26.5 mmol/L urea was added. The flasks were stirred with magnetic stirrers for 4 h in room temperature. The urea concentration of samples from the flasks and from the original dialysis fluid were analyzed in duplicate, and the decrease in urea concentration was used to calculate the amount of urea bound by the carbon, see table below.

| SAMPLE | C urea mmol/L | mean C urea mmol/L | bound urea mmol/g |
|---|---|---|---|
| dialysate | 26.5 | 26.45 | |
| dialysate | 26.4 | | |
| Carbon A | 21.8 | 21.85 | 0.09 |
| Carbon A | 21.9 | | |
| Carbon B | 20.8 | 20.65 | 0.12 |
| Carbon B | 20.5 | | |
| Carbon C | 20.1 | 20.05 | 0.13 |
| Carbon C | 20 | | |

EXAMPLE II 5 g of activated carbon was weighed in three flasks. To each flask, 50 mL of 18 mmol/L solution of urea in water was added. Each flask was kept at different temperatures, one in 2° C. in an ice-water bath, one in room temperature and one in a 37° C. heating cabinet. The flasks were stirred by magnetic stirrers for 2.5 h. The urea concentration of samples from the flasks and from the original urea solution were analyzed in duplicate, and the decrease in urea concentration was used to calculate the amount of urea bound by the carbon, see table below.

| SAMPLE | C urea mmol/L | mean C urea mmol/L | bound urea mmol/g |
|---|---|---|---|
| urea solution | 17.2 | 17.05 | |
| urea solution | 16.9 | | |
| 2° C. | 8 | 8.1 | 0.09 |
| 2° C. | 8.2 | | |
| room temp. | 11 | 10.95 | 0.06 |
| room temp. | 10.9 | | |
| 37° C. | 11.9 | 11.95 | 0.05 |
| 37° C. | 12 | | |

EXAMPLE III 300 g of activated carbon X and activated carbon Y was filled in 800 mL cylindrical Plexiglas flow columns. Spent dialysis fluid from peritoneal dialysis patient was pumped through the columns at a flow rate of 16 ml/min by means of peristaltic pumps. Samples of the fluid were taken at the outlets of the columns at different time points during 3 hours. The urea concentration in the samples from the outlet and a sample of the dialysis fluid pumped into the column was analyzed, and the time-course of urea concentration at the column outlet was plotted. The concentration of urea in the dialysis fluid pumped into the columns is depicted as a dotted line. The total amount of urea bound by the activated carbons was calculated by integration of the area between the urea time-course graph and the dotted line, taking into account the flow rate of the fluid. The total urea binding was 31.2 mmol for carbon X and 28.5 mmol for carbon Y, giving a specific urea binding of 0.104 mmol/g and 0.095 mmol/g activated carbon, respectively.

It is desired to remove about 175 mmol urea per day. If the cartridge is used during four hours and then replaced four times per day, each cartridge should remove 30 mmol urea, which requires about 300 gram of activated carbon per cartridge. In addition, urea is removed by the drained fluid.

Since a filter is arranged between the dialysis fluid and the cartridge, the filter will prevent albumin and other proteins from reaching the cartridge. Thus, no albumin or only a small amount of albumin is lost due to any binding to activated carbon. The filter also operates as a microbiologic filter, whereby the fluids and material at the outer side of the filter may not be required to be sterile. In addition, any particles leaking from the cartridge is stopped by the filter.

Another issue is phosphate removal from dialysis fluid, during peritoneal dialysis as well as hemodialysis. Hyperphosphatemia is a common condition among patients with renal failure. Removal of phosphate through conventional dialysis is often not adequate, and phosphate levels must be further controlled by limiting dietary intake and using oral phosphate binders. In a system where dialysis fluid is regenerated and recirculated, phosphate needs to be continuously removed from the dialysis fluid in order to keep the concentration gradient of phosphate over the dialysis membrane high, and contribute to removal of phosphate from the patient's blood as efficiently as possible.

Current clinically used oral phosphate binders include for example Sevelamer, a polyallylamine polymer, lanthanum carbonate, and calcium acetate/potassium carbonate. Lanthanum carbonate is a highly insoluble lanthanum salt, which becomes somewhat more soluble in the conditions of the digestive tract, releasing free lanthanum ions. As lanthanum phosphate has an even lower solubility, phosphate ions originating from food are precipitated as lanthanum phosphate, with the lanthanum ions released from lanthanum carbonate. The precipitated phosphate is retained within the digestive tract, and thus the phosphate is removed from the body without increasing systemic phosphate levels.

Lanthanum also has other applications as a phosphate sequestering agent, for example in remediation of phosphate-overloaded lakes, a common problem in agricultural areas where phosphate-based fertilizers leach into rivers and lakes. In this case, lanthanum ions may be bound to bentonite, an aluminum-silicate clay with ion-exchange properties. The lanthanum-bentonite is added to the lake water, and the lanthanum ions capture phosphate ions by formation of highly insoluble $LaPO_4$, which sinks to the bottom of the lake. The phosphate is thus sequestered and immobilized in the bottom sediment in an insoluble, biologically unavailable form.

The poor aqueous solubility of lanthanum phosphate, as well as other metal phosphate salts may be exploited for removal of phosphate from a dialysis fluid in a dialysis fluid regeneration system. However, addition of free metal ions to the fluid in the form of a soluble metal salt, or release from an ion-exchanger is not feasible as the ions might diffuse into the patient's blood before precipitating with phosphate. Free metal ions may have severely toxic systemic effects on the patient. In addition, the insoluble metal-phosphate precipitate particles that would form in the fluid could block filters in the fluid path, and, in the case of peritoneal dialysis fluid, may cause irritation of the peritoneal membrane and may be taken up by the afferent lymphatic system, potentially causing unpredictable biological effects.

To solve this problem, there is provided a way to bind phosphate ions on an immobilized metal ion retained on a polystyrene-based resin, which has not previously been described. The dialysis fluid is recirculated through a bed of the resin and phosphate ions are bound to the immobilized metal ion due to the low solubility of the metal-phosphate, which would form an insoluble salt if present free in aqueous solution. In this way, the metal ion is never released into the dialysis fluid and the phosphate binds to the metal ion, and is thus retained in the resin.

In order to bind a metal ion such as lanthanum onto a polystyrene resin with minimal leakage, a resin containing a metal chelating ligand is used. As is well known in the art, polyvalent metal ions can readily complex with iminodiacetic acid (IDA) by bonding with the two carboxylic acid groups. Additionally, a bond with the nearby imino-functionality further strengthens the complex.

Iminodiacetic acid forming a complex with a metal ion (M).

In comparison with ordinary cation exchangers, the IDA ligand is highly selective for metal ions and has a much higher bond strength, giving a very stable binding of metal ions at basic, neutral and slightly acidic pH. Only at very low pH (around or below 2), the metal ions are released and exchanged for $H^+$. Polystyrene resins with IDA ligand are commercially available, and used in metal recovery from ores, galvanic plating solutions, pickling baths and effluents. Grades for removal of heavy metals from potable water are also available. Resins with other metal chelating ligands may also be used, f.ex. phosphonate ligand, ethylene diamine ligand or bis-picolylamine ligand. The polystyrene 'backbone' of the resin could be replaced by other resin-forming polymers that can be functionalized with metal chelating ligands.

Metal ions can be bound on polystyrene resin with IDA ligand (or other metal chelating ligand) by soaking the resin in a solution of a soluble metal salt, for example $CuCl_2$, $ZnCl_2$, $MnCl_2$, $SnCl_2$, $NiCl_2$, $FeCl_2$, $FeCl_3$, $LaCl_3$, $ZnSO_4$, $NiSO_4$, $MnSO_4$, $SnSO_4$, $CuSO_4$, $FeSO_4$, $Fe_2(SO_4)_3$. The concentration and volume of the soaking solution is chosen such that a surplus of metal ions with respect to number of IDA ligands on the resin, is available. The soaking is continued for an appropriate time to allow all IDA ligands to bind with the metal ion, for example 0.5-4 hours. A orbital shaker or other means of agitating the suspension of resin in the solution may be used. The metal solution can be separated from the resin by decanting or filtration. The resin may be washed with water several times in order to remove excess metal ions that are not bound on IDA ligands. After washing, the resin may be dried.

Another method to bind metal onto the resin is to use a flow system, where the resin is contained in a flow-path (f.ex. a cylindrical column), and a solution of metal salt is pumped along the flow path. After binding, water may be pumped through the system to remove any excess metal ions. The resin may be removed from the flow system and dried, or used directly for phosphate binding by flowing the dialysis fluid to be regenerated through the resin.

The dried resin can be incorporated in the dialysis cartridge described earlier, in an amount sufficient for binding the required amount of phosphate ion.

Metal ions bound to chelating ligands on a polymeric resin may leak out of the resin into the fluid surrounding the resin. The leakage depends on the affinity of the metal for the resin in the particular conditions of the surrounding fluid. The higher the affinity, the lower the leakage. To prevent metal ions that detach from the resin from leaking out of the cartridge, an adsorbent that will bind free metal ions can be placed downstream of the phosphate-binding adsorbent containing metal ions. Such an adsorbent may be identical to the metal-chelating resin used to create a phosphate-binding resin by addition of a metal ion, or it may be a resin with another metal chelating ligand. This metal-adsorbing resin will re-capture any metal ions that may leak from the phosphate-binding resin, and prevent them from exiting the cartridge and reaching the patient.

The metal-chelating resin may additionally be utilized for pH modification. Activated carbon may cause an elevation of the pH of dialysis fluid being contacted with the carbon. In order to restore the pH, hydrogen ions may be released from the metal-chelating adsorbent. For this, the metal-chelating adsorbent should contain hydrogen ions bound to the chelating site. In the case of IDA-ligand, hydrogen would be bound on the two acid groups of imino-diacetic acid, see above. The proportion of hydrogen ions versus for example sodium ions bound on the ligands can be adjusted by mixing resin in the hydrogen form with resin in the sodium form in a proportion matching the need of release of hydrogen ions to counteract the elevation in pH caused by activated carbon.

EXAMPLE 1

Binding of Different Metals on Polystyrene-IDA Resin 200 g of commercially available polystyrene-IDA resin was soaked in 2 L of metal salt solution for 3 hours, on an orbital shaker. A sample of the solution was taken for analysis of residual metal concentration, and the metal salt solution was decanted. The resin was washed 5 times with tap water by decanting, and then transferred to a sieve with a mesh size small enough to retain all resin particles. The resin in the sieve was rinsed under running water for around 5 minutes. The resin was transferred to a container with 2.5 L de-ionized ultrapure water, and agitated on an orbital shaker. The rinsing procedure in the sieve was repeated twice daily and the resin was placed in fresh ultrapure water after each rinsing. The washing procedure continued for 4-8 days, and thereafter the resin was dried for 3 days in 40° C., until the moisture content was <10%. The amount of metal ion bound on the resin was calculated from the initial metal salt concentration, the concentration of the metal at the end of the soaking time and the initial weight of the resin.

| Metal salt | Initial conc. (mmol/L) | Residual conc. (mmol/L) | Volume (L) | Amount resin (g) | Metal binding (mmol/g) |
|---|---|---|---|---|---|
| $FeSO_4$ | 200 | 110.1 | 2 | 200 | 0.9 |
| $Fe_2(SO_4)_3$ | 400 | 192.7 | 1 | 100 | 2.1 |
| $CuSO_4$ | 200 | 99.3 | 2 | 200 | 1.0 |
| $LaCl_3$ | 200 | 133.1 | 2 | 200 | 0.7 |
| $MnSO_4$ | 200 | 107.3 | 2 | 200 | 0.9 |
| $ZnSO_4$ | 200 | 106.4 | 2 | 200 | 0.9 |
| $FeCl_2$ | 200 | 123.7 | 2 | 200 | 0.8 |
| $FeCl_3$ | 100 | 38.0 | 2 | 200 | 0.6 |
| $CuCl_2$ | 200 | 98.4 | 2 | 200 | 1.0 |
| $MnCl_2$ | 200 | 111.3 | 2 | 200 | 0.9 |
| $ZnCl_2$ | 200 | 96.2 | 2 | 200 | 1.0 |

The amount of metal bound on the resin did not differ substantially at the concentration of 200 mmol/L. However, in the case of varying concentration of Fe (100-400 mmol/L), the amount of metal bound correlated strongly with the concentration.

EXAMPLE 2

Binding of Phosphate on Polystyrene-IDA-Metal Resin 1 g of each polystyrene-IDA-metal resin described in example 1 was weighed in a 250 mL e-flask. To each flask 200 mL of spent peritoneal dialysis (PD) fluid donated by a PD patient, containing 3 mmol/L phosphate, was added. The flasks were agitated on an orbital shaker in 37° C. for four hours. Samples for determination of phosphate concentration were taken from the initial PD fluid, and after four hours of soaking the resin. Phosphate binding was calculated from the difference in initial and final phosphate concentration, the fluid volume and the amount of resin used.

| Sample/<br>metal salt on<br>resin | Phosphate<br>conc.<br>(mmol/L) | Phosphate<br>binding<br>(mmol/g) |
|---|---|---|
| Test 1: | | |
| Initial PD fluid | 3.16 | N/A |
| $FeSO_4$ (FeII) | 1.72 | 0.29 |
| $Fe_2(SO_4)_3$ (FeIII) | 1.53 | 0.33 |
| $CuSO_4$ | 3.0 | 0.03 |
| $LaCl_3$ | 1.92 | 0.25 |
| $MnSO_4$ | 1.89 | 0.25 |
| $ZnSO_4$ | 2.72 | 0.09 |
| Test 2: | | |
| Initial PD fluid | 3.0 | N/A |
| $FeCl_2$ (FeII) | 1.86 | 0.23 |
| $FeCl_3$ (FeIII) | 2.38 | 0.12 |
| $CuCl_2$ | 2.8 | 0.04 |
| $MnCl_2$ | 2.11 | 0.18 |
| $ZnCl_2$ | 2.4 | 0.12 |

It is evident that resins with bound Fe, La and Mn give a higher phosphate binding compared to Cu and Zn. It was noted that the PD fluid in the flasks with the Mn-resins, and to a lower extent the Zn-resins, was cloudy and apparently contained a precipitate which could be due to leaching of free metal ions from the resin that would precipitate with the phosphate in the fluid. Such leaching and precipitation would remove phosphate from the fluid and give a false high measure of phosphate binding.

The affinity of the IDA ligand for different metals differs, which reflects the tendency of the metal ion to detach from the ligand and leach into the fluid. The affinity is affected by conditions of the surrounding fluid, with respect to parameters such as pH, ionic strength and the presence of other complex-forming substances. In general, the affinity order of the metals tested above is reported to be $Cu^{2+}>Fe^{3+}>Zn^{2+}>Fe^{2+}>Mn^{2+}$. The lower affinity of the ligand for Mn supports the hypothesis of leaching and Mn-phosphate precipitation.

EXAMPLE 3

Binding of Phosphate in a Flow-Column

Figure 5:
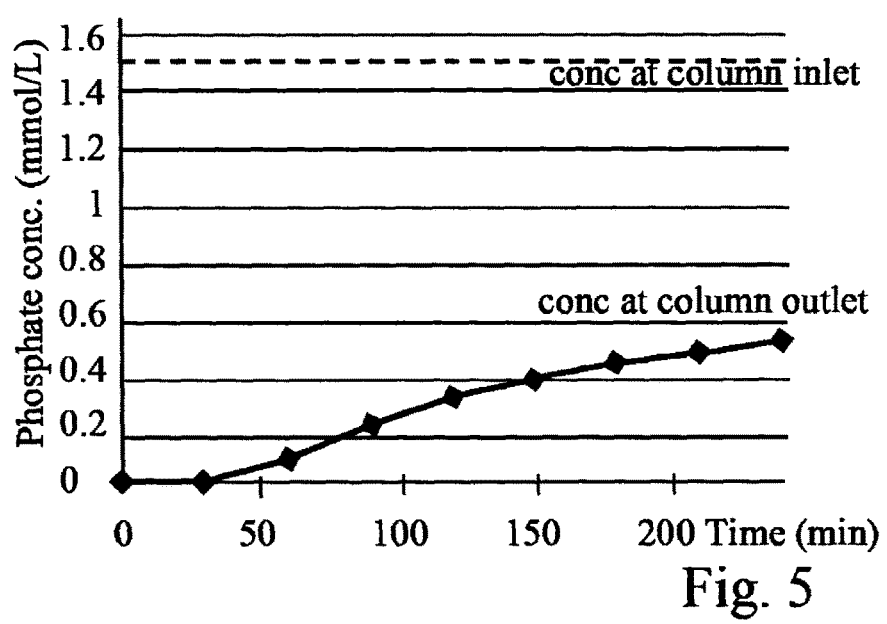
FIG. 5 is a diagram showing the phosphate concentrations.

A cylindrical plexiglass column (Ø2.1 cm, length 19 cm) was filled with 30 g of dry polystyrene-IDA-metal resin. PD fluid containing around 1.5 mmol/L phosphate was pumped through the column at a flow rate of 1 L/h, for 4 hours. Samples for phosphate analysis were taken every 30 min from the outlet of the column. Samples for analysis of metal concentration were taken from the collected volume of fluid that had passed through the column at the end of the test. The amount of phosphate bound in the column was calculated by integration of the concentration profile of phosphate in the outlet fluid with respect to volume of fluid passed through the system (see diagram in FIG. 5).

The diagram shows the phosphate concentration results from the test described above using polystyrene-IDA-Fe resin derived from soaking polystyrene-IDA resin in $Fe_2(SO_4)_3$ solution. The dotted line indicates the phosphate concentration of the fluid pumped into the column, the solid line is the phosphate concentration measured from samples of the outlet fluid, and the shaded area represent the integration of phosphate concentration with respect to time, which can be converted to volume of fluid when the flow rate is known. From this calculation the molar amount of phosphate bound in the column can be derived.

The test was repeated with resins with different metals bound to the IDA ligand. The results are tabulated below.

| Metal salt bound on<br>resin | Phosphate bound in<br>column<br>(mmol) | Metal conc. in collected<br>fluid<br>(mg/L) |
|---|---|---|
| $Fe_2(SO_4)_3$ (FeIII) | 4.9 | 4.7 |
| $LaCl_3$ | 4.2 | 0.16 |
| $FeSO_4$ (FeII) | 3.3 | 4.1 |
| $FeCl_2$ (FeII) | 3.1 | 2.2 |
| $CuCl_2$ | 0.22 | 29 |
| $MnSO_4$ | N/A (precipitation) | 20.7 |
| $ZnCl_2$ | N/A (precipitation) | 9.4 |

The outlet fluid from the resins containing Mn and Zn were turbid and clearly contained a precipitate. For these resins, the time-course of the phosphate concentration in the outlet fluid differed from the expected shape of a gradually saturating adsorbent, but resembled a straight line around a concentration of 0.8 mmol/L for Mn-resin and 1.2 mmol/L for Zn-resin. This indicates that phosphate was not removed by binding on the resin, but by precipitation with leaching metal ions, and thus a calculation of phosphate bound in the resin was not appropriate. Despite the presence of precipitated metal-phosphate in the outlet fluid (which was filtered out before analysis of metal concentration), the concentration of leaching free Mn and Zn in the collected fluid was high.

EXAMPLE 4

Comparison of La and Fe(III) Ion on Polystyrene-IDA Resin

The two metal ligands of polystyrene-IDA resin giving the highest phosphate binding in the flow column test were La(III) and Fe(III) (see example 3). From the results in example 3, Fe(III) stands out as the ligand giving the highest phosphate binding. However, the resins of example 3 were prepared from different metal salts (La(III) resin from $LaCl_3$ and Fe(III) resin from $Fe_2(SO_4)_3$, and the concentration of the metal solution during binding on the resin differed (200 mmol/L of $LaCl_3$, and 400 mmol/L of $Fe_2(SO_4)_3$).

To compare the two metal ligands under equal conditions, the binding of metal on polystyrene-IDA resin was repeated using 200 mmol/L of $LaCl_3$ and 200 mmol/L $FeCl_3$ in the binding procedure described in example 1. 30 g of each of the resins was incorporated in a dialysis cartridge, described above as part of the invention. The cartridge also contained equal amounts of an ion exchanger for potassium binding, an activated carbon for binding of urea and creatinine.

PD fluid containing around 1.5 mmol/L phosphate, 20 mmol/L urea, 3.5 mmol/L potassium ion and 1 mmol/L creatinine, was pumped through the cartridge at a flow rate of 1 L/h, for 4 hours. Samples for analysis of phosphate, urea, potassium and creatinine were taken every 30 min from the outlet of the cartridge. Samples for analysis of metal concentration were taken from the collected volume of fluid that had passed through the cartridge at the end of the test.

The amount of substances bound by the cartridges are summarized in the table below.

| Substance | Cartridge with Fe-resin amount bound (mmol) | Cartridge with La-resin Amount bound (mmol) |
| --- | --- | --- |
| Phosphate | 4.2 | 5.0 |
| Urea | 33 | 33 |
| Creatinine | 4.1 | 4.2 |
| Potassium | 5.2 | 5.1 |

The leakage of metal ligand from the purification cartridges was analyzed from a sample of the collected PD fluid that had passed the column during the 4-hour test, see table below.

| Cartridge | La conc. (µg/L) | Fe conc. (mg/L) |
| --- | --- | --- |
| Fe-resin | n.d. | 10.8 |
| La-resin | 0.3 | n.d. |

In this comparison, the cartridge with the La-resin bound 0.8 mmol more phosphate than the cartridge with Fe-resin. Metal leakage from the cartridge was several orders of magnitude higher from the Fe-resin containing cartridge than the La-resin containing cartridge.

EXAMPLE 5

Binding of Leaking La Ion from Phosphate Binder on Metal Chelating Resin

A cylindrical plexiglass column (Ø2.1 cm, length 19 cm) was filled with 30 g of dry polystyrene-IDA-La resin. A similar but shorter column (Ø2.1 cm, length 10 cm) was filled with 10 g of dry polystyrene-IDA resin, and connected after the first column using silicone tubing and a sampling port. PD fluid was pumped through the serially connected columns at a flow rate of 1 L/h, for 4 hours. Samples from the outlet of the second column and from the sampling port between the columns were taken at several time-points, and the La concentration was analyzed. The results are presented in the table below.

| Sampling time (min) | La conc. after first column (mg/L) | La conc. after second column (mg/L) |
| --- | --- | --- |
| 0 | 3.03 | 0.033 |
| 20 | 1.08 | 0.017 |
| 60 | 0.92 | 0.008 |
| 240 | 0.022 | <0.001 |

The concentration of leaching La from the first column was highest in the beginning of the test and decreased about 100-fold during 4 hours (240 min). The second column containing the metal-chelating resin decreased the La concentration in the outlet of the first column around 100-fold at 0 and 20 min, and 1000-fold at 60 min. At the 4-hour time point the concentration of La in the outlet of the second column was below the detection limit of the analysis.

The results gained from the tests described in the examples showed that phosphate can be bound on a metal ion that is held on a polystyrene resin by means of the chelating ligand IDA, and in this way phosphate can be removed from PD fluid. The results also led to the unexpected discovery that 3-valent metal ions such as $Fe^{3+}$ and $La^{3+}$ give the highest phosphate binding, when immobilized on a polystyrene-IDA resin. The leaching of metal ion from the resin in PD fluid did not correspond to the affinity order generally described for the IDA ligand, but surprisingly Cu was most prone to leaching, followed by Mn and Zn, which should have a lower affinity for IDA than Cu, as mentioned above. Leaching of Fe was lower than the three metals mentioned, but substantially higher than leaching of La, which was the tightest bound metal ion under these conditions. Evidently, the specific chemical environment of spent PD fluid gives an altered affinity of metal ions for the IDA ligand, which cannot be predicted from the generally prevailing understanding of the affinity order mentioned in example 2. Release of leaching metal ions from an adsorbent cartridge can be reduced by incorporating a metal-chelating resin downstreams of the phosphate-binding resin, as shown in example 5.

In the claims, the term "comprises/comprising" does not exclude the presence of other elements or steps. Furthermore, although individually listed, a plurality of means, elements or method steps may be implemented by e.g. a single unit. Additionally, although individual features may be included in different claims or embodiments, these may possibly advantageously be combined, and the inclusion in different claims does not imply that a combination of features is not feasible and/or advantageous. In addition, singular references do not exclude a plurality. The terms "a", "an", "first", "second" etc. do not preclude a plurality. Reference signs in the claims are provided merely as a clarifying example and shall not be construed as limiting the scope of the claims in any way.

Although the present invention has been described above with reference to specific embodiment and experiments, it is not intended to be limited to the specific form set forth herein. Rather, the invention is limited only by the accompanying claims and, other embodiments than those specified above are equally possible within the scope of these appended claims.

The invention claimed is:

1. An apparatus for performing adsorbent dialysis, comprising:
   a cartridge configured for adsorbent dialysis, the cartridge including,
      a container, at least a portion of which is made of flexible plastic sheets forming an interior space of the container having a variable volume;
      a powder material, being arranged for adsorbent dialysis and comprising activated carbon, said powder material being non-dissolvable, wherein said powder material is filled into said interior space in a dry state and so that substantially all of the interior space is occupied by the powder material;

a purification fluid provided in the interior space surrounding the powder material;

an inlet tube and an outlet tube arranged for passing said purification fluid into and out of said interior space for passage of said purification fluid through said powder material for regeneration of said purification fluid;

a filter constructed for preventing said power material from leaving the cartridge during said passage of said purification fluid;

a meander-like space forming meander-like flow paths being formed by the flexible plastic sheets;

a sub-pressure lower than ambient pressure being provided in the interior space so that the powder material is immobilized and stiff in the purification fluid by said sub-pressure inside the interior space;

said flexible plastic sheets under said sub-pressure being sucked against the powder material, resulting in that no preferential flow paths are established; and no preferential flow paths are formed adjacent the flexible material in the cartridge; said apparatus further comprising:

a pump; and a pressure reducing valve for passing said purification fluid through the cartridge for adsorbent dialysis by circulation of said purification fluid through the cartridge at the sub-pressure in said interior space, which sub-pressure in said interior space is at least 50 mbar below ambient pressure.

2. A cartridge for adsorbent dialysis, the cartridge being configured to perform adsorbent dialysis, comprising:

a container at least a portion of which is made of flexible plastic sheets forming an interior space of the container having a variable volume, a powder material being arranged for adsorbent dialysis and comprising activated carbon, said powder material being non-dissolvable, when substantially all of said interior space is occupied by the powder material;

a purification fluid provided in the container and surrounding the powder material;

an inlet tube and an outlet tube constructed for passage of said purification fluid into and out of the container;

a filter constructed for preventing said powder material from leaving the cartridge during said passage of said purification fluid;

wherein during operation the cartridge being provided with a sub-pressure lower than ambient pressure so that the powder material is immobilized and stiff by said sub-pressure inside the interior space and in the purification fluid and wherein said flexible plastic sheets under said sub-pressure being sucked against the powder material, resulting in that no preferential flow paths are established and no preferential flow paths are formed adjacent the flexible material in the cartridge.

3. The cartridge according to claim 2, wherein a pressure reducing valve is arranged at said inlet tube for lowering pressure at said inlet tube.

4. The cartridge according to claim 3, wherein said pressure reducing valve is arranged integrally with said cartridge.

5. The cartridge according to claim 3, wherein said pressure reducing valve is arranged to reduce pressure by at least 50 mbar.

6. The cartridge according to claim 3, wherein said pressure reducing valve is adjustable for reducing pressure by at least one of: 50 mbar, 100 mbar, 150 mbar, 200 mbar and 500 mbar at passage of a liquid through said pressure reducing valve.

7. The cartridge according to claim 2, wherein said powder material further comprises at least one of: a phosphate adsorbent and a potassium adsorbent.

8. The apparatus according to claim 1, wherein said adsorbent dialysis powder material further comprises at least one of:

a phosphate adsorbent; and a potassium adsorbent.

9. The apparatus according to claim 1, wherein a pressure reducing valve is arranged at said inlet tube for reducing pressure at the inlet tube.

10. The apparatus according to claim 9, wherein said pressure reducing valve is arranged to reduce pressure by at least 50 mbar.

11. The apparatus according to claim 9, wherein said pressure reducing valve is adjustable for reducing pressure by one of: 50 mbar, 100 mbar, 150 mbar, 200 mbar or 500 mbar at passage of a fluid through said pressure reducing valve.

* * * * *